United States Patent [19]

Ackerman et al.

[11] Patent Number: 4,684,883
[45] Date of Patent: Aug. 4, 1987

[54] METHOD OF MANUFACTURING HIGH-QUALITY SEMICONDUCTOR LIGHT-EMITTING DEVICES

[75] Inventors: David A. Ackerman, Hopewell; Renato M. Camarda, Fanwood; Robert L. Hartman, Warren, all of N.J.; Magaly Spector, Wyomissing, Pa.

[73] Assignee: American Telephone and Telegraph Company, AT&T Bell Laboratories, Murray Hill, N.J.

[21] Appl. No.: 733,047

[22] Filed: May 13, 1985

[51] Int. Cl.[4] .................. G01N 27/00; G01J 1/00; H01J 3/14

[52] U.S. Cl. .................. 324/71.5; 324/158 R; 324/158 D; 356/237; 356/121; 250/234

[58] Field of Search .................. 324/158 D, 71.5; 357/17; 356/121; 250/442.1, 234; 356/237

[56] References Cited

U.S. PATENT DOCUMENTS 4,002,975 1/1977 Erickson et al. .................. 324/96 X
4,063,103 12/1977 Sumi .................. 250/398 X
4,160,598 7/1979 Firester et al. .................. 356/121

OTHER PUBLICATIONS

T. L. Paoli, "Nonlinearities in the Emission Characteristics of Stripe-Geometry (AlGa) As Double-Heterostructure Junction Lasers", *IEEE Journal of Quantum Electronics*, vol. QE-12, No. 12, Dec. 1976, pp. 770-776.
H. C. Casey, Jr. et al, *Heterostructure Lasers*, Part B, Academic Press, 1978, pp. 207-217 and 240-242.
E. Oomura et al, "Transverse Mode Control in InGaAsP/InP Buried Crescent Diode Lasers", *Electronics Letters*, vol. 17, No. 1, Jan. 8, 1981, pp. 83-84.
D. Botez, "InGaAsP/InP Double-Heterostructure Lasers: Simple Expressions for Wave Confinement, Beamwidth, and Threshold Current over Wide Ranges in Wavelength (1.1-1.65 μm)," *IEEE Journal of Quantum Electronics*, vol. QE-17, No. 2, Feb. 1981, pp. 178-186.
K. Mizuishi et al, "Reliability of InGaAsP/InP Buried Heterostructure 1.3 μm Lasers," IEEE Journal of Quantum Electronics, vol. QE-19, No. 7, Jul., 1983, pp. 1294-1301.
N. K. Dutta et al, "Criterion for Improved Linearity of 1.3 μm InGaAsP-InP Buried-Heterostructure Lasers", *Journal of Lightwave Technology*, vol. LT-2, No. 2, Apr. 1984, pp. 160-164.

Primary Examiner—Reinhard J. Eisenzopf
Assistant Examiner—Vinh P. Nguyen
Attorney, Agent, or Firm—Lester H. Birnbaum

[57] ABSTRACT

A nondestructive method is proposed for measuring stripe dimensions in order to grade light-emitting structures such as lasers. The width of the near-field emission parallel to the stripe is measured while the laser is operating below threshold. This measurement is correlated with the actual stripe width and with the possibility of kinks developing in the light output. The width of the far-field emission perpendicular to the junction plane can also be measured, and the product of the two widths can be correlated with the stripe area and the possibility of kinks in the laser output.

8 Claims, 9 Drawing Figures

METHOD OF MANUFACTURING HIGH-QUALITY SEMICONDUCTOR LIGHT-EMITTING DEVICES

BACKGROUND OF THE INVENTION

This invention relates to the manufacture of semiconductor light-emitting devices and, in particular, to the grading of semiconductor lasers for appropriate applications.

Semiconductor lasers currently in use usually include a narrow stripe for light emission. This stripe may be defined by a change in index of refraction across the lateral dimensions of the active layer (index guided structure) or by current confinement within the desired portion of the active layer (gain guided structure). The stripe may comprise the entire width of the active region surrounded by high bandgap material or comprise only a portion of the active region. (See, for example, Casey and Panish, *Heterostructure Lasers*, Part B, pp. 207–217 and 240–242, Academic Press, 1978.)

Semiconductor lasers can exhibit nonlinearities or "kinks" in their light output versus current characteristic. The presence of such kinks could disqualify the laser from use in systems requiring high accuracy. Thus, detecting kinks in the light output can be a critical step in reliability. To make matters worse, it is hypothesized that some devices may not exhibit the kink until after field installation when it becomes difficult or impossible to replace the laser. It is, therefore, highly desirable during the manufacturing process to be able to identify devices which exhibit or have the potential for exhibiting kinks in their output. This identification could be done on final device structures. However, it would also be highly beneficial to identify problems early in the fabrication stage to avoid costly processing. For example, if defects could be detected during the wafer state of processing, subsequent metallizations and cleaving could be avoided for unsuitable devices.

It has been suggested that the appearance of kinks depends upon stripe width and stripe thickness (see, e.g., Paoli, "Nonlinearities in the Emission Characteristics of Stripe-Geometry AlGaAs Double Heterostructure Junction Lasers," *IEEE Journal of Quantum Electronics*, Vol. QE-12, pp. 770–776 (1976), and Dutta et al, *Journal of Lightwave Technology*, Vol. LT-2, pp. 160–164 (1984)). In addition, other phenomena which adversely affect laser performance, such as beam wander, may be correlated with the size of the stripe. Thus, a measure of stripe width and thickness could provide a means for determining the acceptability of a laser for high reliability applications. In fact, since stripe thickness is easier to control during laser fabrication, a measure of stripe width alone could be used for grading the laser. Unfortunately, the standard method of measuring stripe width involves techniques which destroy the laser facet or could otherwise introduce damage to the laser.

Consequently, it is a primary object of the invention to provide a nondestructive method of measuring the stripe width of light-emitting structures in order to grade the reliability of the final devices.

SUMMARY OF THE INVENTION

This and other objects are achieved in accordance with the invention which is a method of grading the accuracy of the output from a light-emitting stripe geometry structure. An excitation is supplied to the structure so as to produce a spontaneous light emission. The intensity profile of the near-field emission of the structure is measured. The width of the measured intensity profile is then determined, and the laser is graded according to whether the width is above or below a predetermined cut-off value.

BRIEF DESCRIPTION OF THE DRAWING

These and other features of the invention will be delineated in more detail in the following description. In the drawing.

It will be appreciated that for purposes of illustration, these figures are not necessarily drawn to scale.

DETAILED DESCRIPTION

Figure 1:
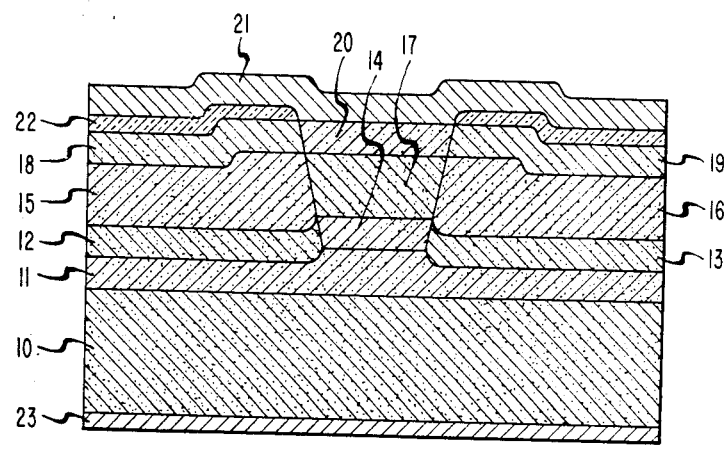
FIG. 1 is a cross-sectional view of a typical laser which can make use of the present invention.

FIG. 1 illustrates, in cross section, a stripe geometry semiconductor laser, generally known as an etched mesa buried heterostructure, which can make use of the invention. It will be appreciated that this structure is an example only, and the invention should be useful for all stripe geometry light-emitting semiconductor devices.

In this example, the laser included a substrate, 10, which was n-type InP. Formed over the substrate was a buffer layer, 11, which was also n-type InP. Blocking layers 12 and 13 comprising p-type InP were formed over the layer 11 on either side of the active region 14. In this example, the active region was InGaAsP with a thickness of 0.2 μm. The stripe width was in the range 1–4 μm.

Layers 15 and 16 comprising n-type InP were formed over the blocking layers 12 and 13, respectively. A p-type InP clad layer, 17, was formed over the active stripe region, 14. The layers, 15 and 16, were capped by layers, 18 and 19, comprising n-type InGaAsP, while layer, 17, was capped by a p-type InGaAsP layer, 20. A layer, 21, of Cr/Au made electrical contact to the p-side of the semiconductor through a window in insulating layer, 22, which was SiO₂. Contact to the substrate was provided by a layer, 23, of Au/Sn.

Figure 2:
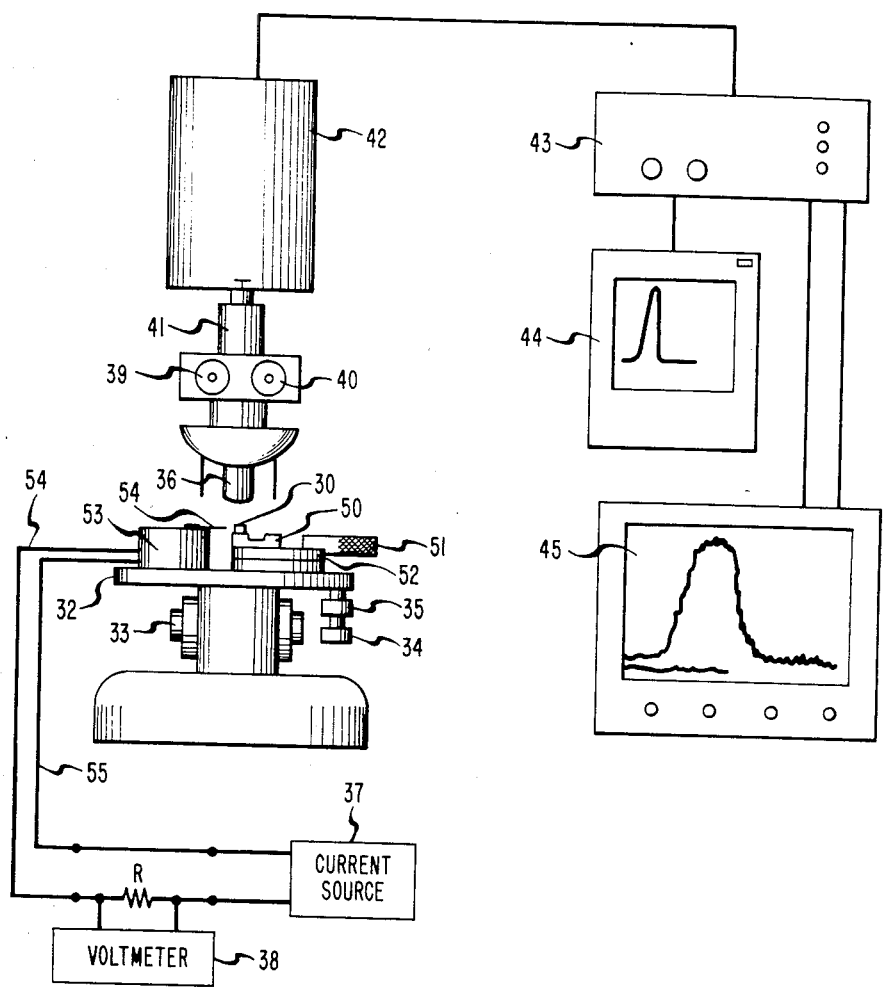
FIG. 2 is a schematic illustration demonstrating a measurement technique which can be used in accordance with one embodiment of the invention.

A schematic illustration of the measurement of near-field emission from such lasers is provided in FIG. 2. The laser, 30, was placed in a cradle, 50, which was mounted on a holder including a stationary portion, 53, and a movable portion 52. A micrometer, 51, provided a fine-tune adjustment of laser position and moved the laser into electrical contact with wires, 54 and 55, which were mounted on the stationary portion of the holder. These wires were coupled to a current source, 37, for driving the laser, while the voltage was monitored across resistor, R, by a voltmeter, 38. The holder was, in turn, mounted on a microscope stage, 32. Attached to the microscope stage were focus knobs, 33, and positioning knobs, 34 and 35, for positioning of the laser in relation to the microscope objective lens, 36.

The laser was viewed through eyepieces 39 and 40 for alignment. A portion of the laser light was projected by lens, 41, into an infrared camera, 42. The camera transmitted the image to a standard video analyzer, 43, which converted the spot from the laser into an intensity profile curve. Coupled to the analyzer was a TV monitor, 44, which displayed the intensity profile of the light output. A standard recorder, 45, was also coupled to the analyzer to produce a permanent recording of the intensity profile in the general form illustrated in the Figure.

Figure 3:
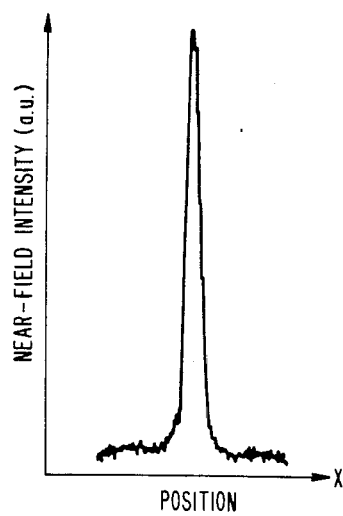
FIGS. 3 and 4 are typical near-field intensity profiles obtained by the technique of FIG. 2.
Figure 4:
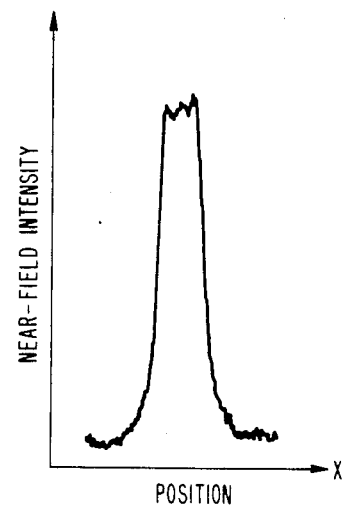

Typical near-field intensity profiles obtained from the above technique while the lasers were driven below threshold levels are illustrated in FIGS. 3 and 4. Both curves show the intensity of light output (in arbitrary units) as a function of lateral position across the width of the stripe (a direction parallel to the junction plane). FIG. 3 is the profile for a laser having a stripe width of 1 μm, while FIG. 4 is a profile from a 3 μm stripe laser.

Figure 5:
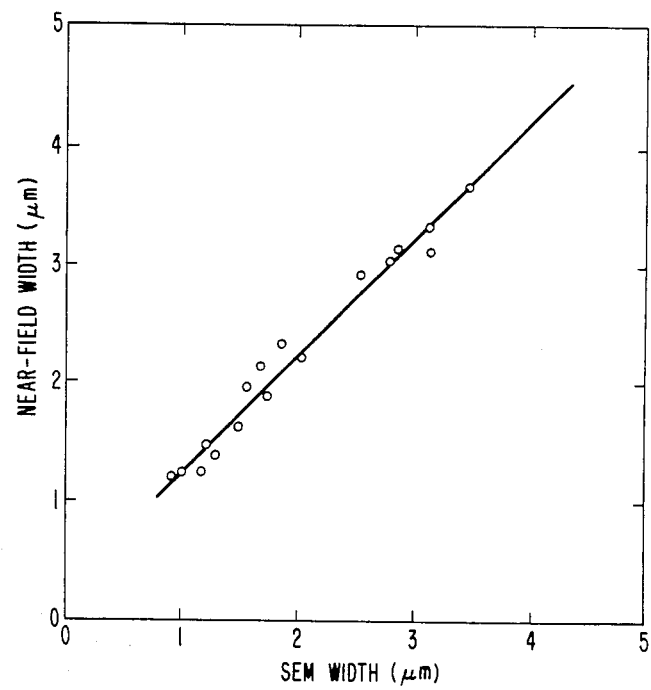
FIG. 5 is a graph correlating the width of the intensity profile with the stripe width of the laser.

The width of the intensity profile of each laser during subthreshold operation was determined by calculating the width of the profile at half its maximum (FWHM). The stripe width of each laser was also determined by Scanning Electron Microscopy (SEM) to provide a standard for comparison of the present inventive technique. The near-field FWHM was shown to have a linear relationship with the SEM-determined stripe width as shown in FIG. 5. For this particular type of laser, the relationship between near-field width ($W_n$) and width determined by SEM measurements ($W_{SEM}$), both in units of micrometers, was found to be $$W_n = 1.012\ W_{SEM} + 0.222. \tag{1}$$

It was determined that for any given near-field width, the uncertainty in the inferred stripe width was $\leq \pm 0.05$ μm.

Figure 6:
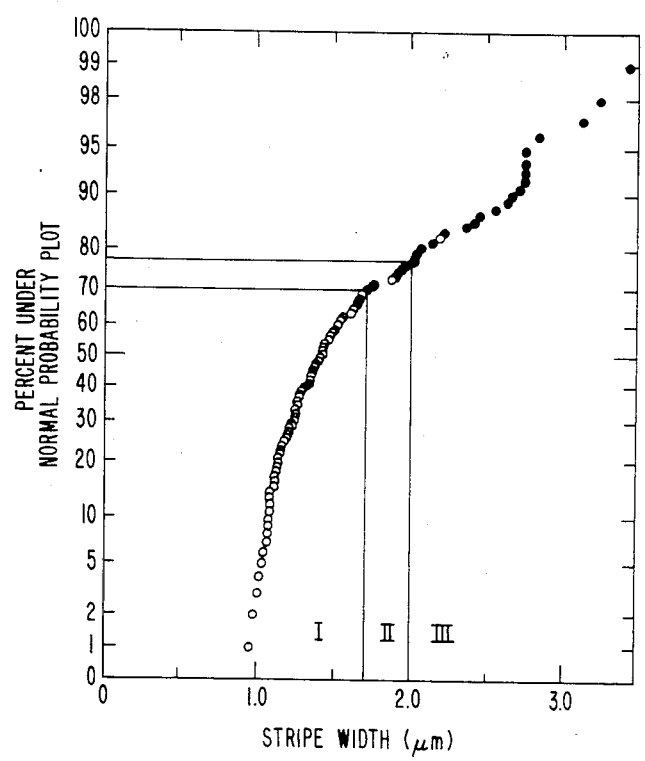
FIG. 6 is a graph correlating the occurrence of kinks in light output as a function of stripe width.

The correlation between the occurrence of kinks and stripe width in the laser of this example is illustrated in FIG. 6. Each dot on the Figure represents one laser, with open dots indicating lasers with no kinks and black dots indicating lasers which exhibited kinks upon initial testing. It is also apparent from FIGS. 5 and 6 that the lasers with kinks (e.g., region III) can be separated from most of the lasers without kinks (e.g., region I) by establishing a cut-off based on near-field width. In this example, the cut-off could be approximately 1.7 μm as determined by near-field FWHM. Thus, during manufacture, any lasers with near-field widths above the cut-off would be presumed to either exhibit kinks or have the potential for exhibiting kinks and therefore be downgraded for uses which do not require high accuracy. Of course, the cut-off point for any particular laser structure can be raised or lowered according to the specifications of the system in which the lasers will be installed. Curves similar to those shown in FIGS. 5 and 6 can be generated for other types of stripe geometry lasers in order to correlate the near-field width, the stripe width, and the occurrence of kinks.

One of the advantages of near-field measurements is that they can be performed well below the laser threshold. In this example, laser threshold was approximately 20 mA, and the measurements were made at a current of approximately 1 mA. Subthreshold operation is important since it eliminates spurious modes which can be present in the light output near or above threshold. The use of a small driving current also insures that the test will be harmless to the laser. It is recommended that the current through the laser during near-field measurement be as small as possible so the spontaneous emission will be dependent essentially only upon stripe width. A recommended maximum is less than 10 percent of threshold, but currents as high as 50 percent might be useful. Near-field measurements are also advantageous since they are not affected by phase shifts across the stripe as is often the case with far-field measurements.

It will be understood that in the context of this application, "near-field" emission is intended to mean the light output within a distance of one wavelength of emitted light from the laser facet.

Figure 7:
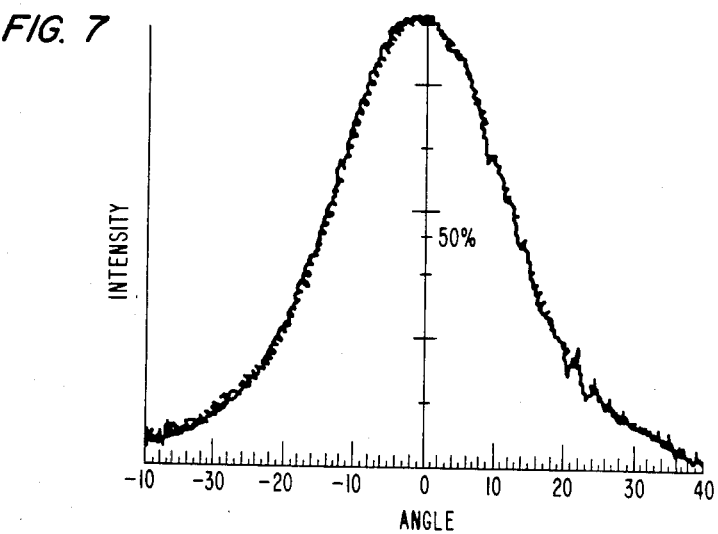
FIG. 7 is a typical far-field intensity profile obtained in accordance with a further embodiment of the invention.
Figure 8:
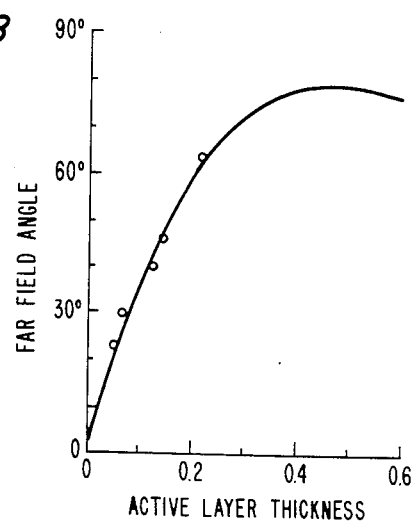
FIG. 8 is a graph correlating the far-field angle with the stripe thickness of the laser.

If further accuracy is desired in grading the lasers (for example, to address those devices in region II of FIG. 6), it is possible to provide additional measurements in order to determine the area of the active stripe rather than just the stripe width. For example, the far-field emission of the laser can be measured with standard apparatus. The intensity profile of the emitted light in the direction perpendicular to the junction plane of the laser can then be derived. A typical profile is illustrated in FIG. 7. The far-field angle, i.e., the angle made by lines drawn from the junction to the half-maximum points of the curve in the plane of measurement, is then calculated. This angle is related to the active layer thickness for the laser of FIG. 1, as shown in the graph of FIG. 8. (The relationship between the far-field angle and active layer thickness is discussed, for example, by Boltz in "InGaAsP/InP Double-Heterostructure Lasers: Simple Expressions for Wave Confinement, Beamwidth, and Threshold Current over Wide Ranges in Wavelength (1.1–1.65 μm)," *IEEE Journal of Quantum Electronics*, Vol. QE-17, No. 2, pp. 178–186 (February 1981).)

Figure 9:
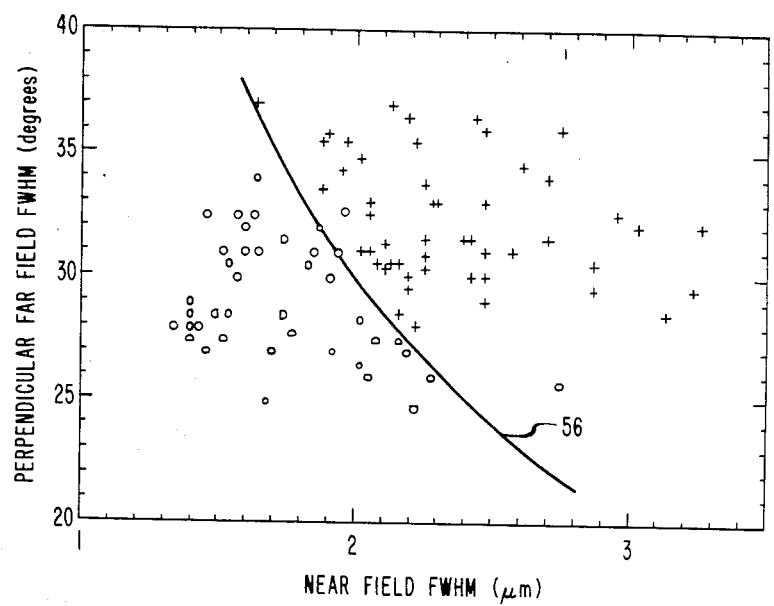
FIG. 9 is a graph of far-field width and near-field width for a group of lasers tested in accordance with said further embodiment.

Since the near-field width at half maximum is proportional to the active layer width and the perpendicular far-field width at half maximum (as represented by the far-field angle) is proportional to the active layer thickness, the product of the two values provides a representation of the active layer area. A cut-off value can therefore be based on this product, rather than stripe width alone, in order to separate lasers without kinks from those with kinks. For example, FIG. 9 shows a distribution of laser devices on a plot of perpendicular far-field width at half maximum and near-field width at half maximum, as determined in accordance with the previously described procedures. Here, lasers without kinks are represented by the symbol "0" and lasers with kinks by the symbol "+". The solid line 56 is a line of constant area which provides a useful cut-off value for separating the lasers tested. In this example, the cut-off value was 60 degrees-microns. Again, the cut-off value can be adjusted according to particular needs, and desirable boundaries can be found empirically for other types of lasers.

While the invention has been described in terms of measuring spontaneous emission from completed stripe geometry laser devices, it should not be considered so limited. Since several lasers are usually fabricated from a single semiconductor wafer, it may be possible to grade all such lasers once semiconductor wafer processing is completed and prior to formation of metallization and cleaving into individual devices. This can be done by any excitation of the semiconductor wafers which will produce spontaneous light emission from the stripe region. This excitation can be electrical, as in the previous example, or emission can be induced by application of an appropriate photo-excitation. Grading can also be done, according to the invention, prior to bonding of the devices to heat sinks, since measurements are made well below threshold. Finally, it may be possible to apply the present invention to light-emitting devices other than lasers, such as edge-emitting light-emitting diodes.

It should be understood, therefore, that in the claims, the term "light-emitting stripe geometry structure" is intended to include any structures from wafers to final devices which spontaneously emit light from a stripe upon an appropriate excitation. The term "excitation" is intended to include photo or electrical pumping of the carriers in the semiconductor to produce light emission. Further, the light-emitting structure is not limited to a laser unless otherwise specified.

Various modifications of the disclosed subject matter will become apparent to those skilled in the art. All such variations which basically rely on the teachings through which the invention has advanced the art are properly considered within the spirit and scope of the invention.

What is claimed is:

1. A method of grading a light-emitting stripe geometry structure having a certain stripe width comprising the steps of:
   applying an excitation to the structure so as to produce a spontaneous light emission having a near-field intensity which is a function of position across the stripe;
   measuring said intensity of the near-field of the spontaneous emission of the light-emitting structure across the stripe to establish a near-field intensity profile having a characteristic width at various intensities;
   determining a width of the measured intensity profile; and
   grading said structure according to whether the width of the intensity profile is above or below a predetermined cut-off value.

2. The method according to claim 1 wherein the width of the intensity profile is determined by measuring the width of the profile at half its maximum intensity.

3. The method according to claim 1 wherein the light-emitting structure is a laser having a lasing threshold, and the light emission is below the lasing threshold.

4. The method according to claim 3 wherein a current is supplied through the laser during the measurement of the intensity of the near-field and said current is less than 10 percent of the lasing threshold.

5. The method according to claim 1 wherein the cut-off value is chosen to determine if the emission will exhibit a kink.

6. The method according to claim 3 wherein the laser is a buried heterostructure laser.

7. The method according to claim 1 where the structure has a far-field emission with an intensity which is a function of position in a direction perpendicular to the plane of the stripe further comprising the steps of:
   measuring said intensity of the far-field emission to establish a far-field intensity profile having a characteristic width at various intensities;
   determining a width of the far-field intensity profile;
   determining a product of said width of the near-field and far-field intensity profiles; and
   grading the structure according to whether the product is above or below a predetermined cut-off value.

8. The method according to claim 7 wherein the width of the second intensity profile is determined by the width of said second intensity profile at half its maximum.

* * * * *